United States Patent [19]

Lafon

[11] 4,049,829
[45] Sept. 20, 1977

[54] SULPHUR CONTAINING HYDROXY ALIPHATIC COMPOUNDS

[75] Inventor: Louis Lafon, Paris, France

[73] Assignee: Societe anonyme dite: Laboratoire L. Lafon, Maisons-Alfort, France

[21] Appl. No.: 614,624

[22] Filed: Sept. 18, 1975

[30] Foreign Application Priority Data

Sept. 23, 1974 United Kingdom ............... 41381/74

[51] Int. Cl.$^2$ ..................... A01N 9/00; C07C 149/18
[52] U.S. Cl. ................................. 424/337; 260/609 R
[58] Field of Search ..................... 260/609 R; 424/337

[56] References Cited

U.S. PATENT DOCUMENTS 3,021,215  2/1962  Williams et al. ................. 260/609 R

FOREIGN PATENT DOCUMENTS 2,146,138  6/1971  France ........................... 260/609 R
1,307,227  8/1969  United Kingdom ............ 260/609 R

OTHER PUBLICATIONS

Chem. Abst. vol. 71 (1969) pp. 66042n.

Primary Examiner—Delbert R. Philips

[57] ABSTRACT

The present invention concerns as new industrial products, hydroxy-thioalkanes of the formula:

HO—A—S—(CH$_2$)$_n$—S—A—OH where $n$ is an integer from 5 to 15 and A is a straight or branched C$_2$-C$_6$ hydrocarbon chain which may also comprise an OH group.

The compounds of formula I are useful in therapeutics, notably as hypolipemiant and hypocholesterolemiant agents.

3 Claims, No Drawings

SULPHUR CONTAINING HYDROXY ALIPHATIC COMPOUNDS

The present invention relates to symmetrical sulphur-containing hydroxy aliphatic compounds. It also relates to the process of preparation of such compounds and their use both in therapeutics particularly as hypolipaemiant and hyperchlolesterolaemiant agents.

The compounds according to the invention correspond to the general formula:

$$HO-A-S-(CH_2)_n-S-A-OH \quad (I)$$

in which $n$ is an integral number from 5 to 15 and the group A is a straight or branched $C_2$-$C_6$ hydrocarbon chain which can include an OH group.

As examples of A, reference may be made to the groups: $CH_2CH_2$, $CH(CH_3)CH_2$, $CH_2CH(CH_3)$, $C(CH_3)_2CH_2$, $CH_2C(CH_3)_2$, $C(CH_3)_2C(CH_3)_2$, $CH_2CHOHCH_2$, $CH(CH_2OH)CH_2CH_2$, $CH_2CH_2CH$ and $CH_2CH(CH_3)CH_2$.

In order to prepare the compounds of Formula I, various synthetic methods are used which are based upon known principles. According to the invention, the following two methods are preferably used:

Method I consists in reducing by means of LiAlH$_4$ a compound of the formula:

$$ROOC-B-S-(CH_2)_n-S-B-COOR \quad (IV)$$

where $n$ is as defined above, R is H or a $C_1$-$C_2$ alkyl group and B is a $C_1$-$C_5$ hydrocarbon chain such that A is BCH$_2$; and Method II consists in reacting an ω,ω'-dihaloalkane of the formula:

$$Hal-(CH_2)_n-Hal \quad (II)$$

where $n$ is as defined above and Hal represents a halogen atom, viz. F, Cl, Br or I, the halogen atom preferably being bromine, with a hydroxymercaptan of the formula:

$$HS-A-OH \quad (III)$$

in alkaline medium, preferably in an alcohol in the presence of 10 N NaOH.

It will be clear that Method II which is applicable irrespective of A is the more general. In contrast, method I can only be used for the synthesis of some of the compounds of formula (I), that is to say those in which A = BCH$_2$.

In order to apply method II with a view to synthesizing the compounds of formula I where A is (CH(CH$_3$)CH$_2$, a new method of preparation, using an intermediate product, 2-mercaptopropanol, has been developed. This is described hereinafter. More precisely, according to the invention there is provided a process for the preparation of compounds of the general formula:

$$HO-CH_2-\underset{CH_3}{\underset{|}{CH}}-S-(CH_2)_n-S-\underset{CH_3}{\underset{|}{CH}}-CH_2-OH \quad (Ia)$$

which comprises the 2-methylthiirane and 2-mercaptopropanol formations, wherein:

a. thiourea is reacted with propylene oxide in acid medium to form a β-hydroxythiouronium salt which is then decomposed in alkaline medium to 2-methylthiirane;

b. the 2-methylthiirane thus obtained is acetylated by means of acetic anhydride to obtain, by opening of the thiirane ring, 2-acetylmercaptopropyl acetate;

c. the 2-acetylmercaptopropyl acetate is treated by methanolysis with CH$_3$OH in the presence of H$^+$ ions to obtain 2-mercaptopropanol; and d. the 2-mercaptopropanol is reacted with a ω,ω'-dihalogenoalkane of Formula II.

The reaction mechanism relating to this process has been schematized hereafter. Details of the operating conditions are given at Example 6A.

a. first stage: synthesis of 2-methylthiirane $$CH_3-CH\underset{O}{\overset{}{\diagdown\diagup}}CH_2 + S=C\underset{NH_2}{\overset{NH_2}{\diagup\diagdown}} \xrightarrow{H^+}{H_2O}$$

$$\left[ CH_3-\underset{OH}{\underset{|}{CH}}-CH_2-S-C\underset{NH_2}{\overset{NH_2}{\diagdown\diagup}} \right]^+$$

b. second stage: acetylation of 2-methylthiirane $$CH_3-CH\underset{S}{\overset{}{\diagdown\diagup}}CH_2 + (CH_3CO)_2O \xrightarrow{C_5H_5N}$$

$$CH_3-\underset{\underset{CO-CH_3}{\underset{|}{S}}}{\underset{|}{CH}}-CH_2-O-CO-CH_3$$

Note: It is essential that the acetylation is effected with acetic anhydride. In fact, acetylation with CH$_3$COCl does not give 2-acetylmercaptopropyl acetate but the isomer of this product, namely 1-acetylmercapto-2-propyl acetate of the formula:

$$CH_3-\underset{O-CO-CH_3}{\underset{|}{CH}}-CH_2-S-CO-CH_3$$

because experience shows that (CH$_3$CO)$_2$O and CH$_3$COCl lead to different openings of the 2-methylthiirane ring.

c. third stage: methanolysis of 2-acetylmercaptopropyl acetate $$CH_3-\underset{S-CO-CH_3}{\underset{|}{CH}}-CH_2-O-CO-CH_3 + 2CH_3OH \xrightarrow[CH_3OH]{H^+}$$

$$CH_3-\underset{SH}{\underset{|}{CH}}-CH_2OH + 2CH_3CO_2CH_3$$

d. fourth stage: condensation of the 2-mercaptopropanol with a ω,ω'-dihaloalkane $$2CH_3-\underset{SH}{\underset{|}{CH}}-CH_2OH + Hal-(CH_2)_n-Hal \longrightarrow \quad (Ia)$$

In Table I below, a certain number of compounds according to the invention are summarised in a non-limitative fashion.

These products have been prepared as indicated in the following Examples.

EXAMPLE 1

2,2,15,15-Tetramethyl-3,14-dithia-1,16-hexadecanediol

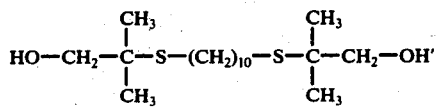

Code No. 40 055

A solution of 21.6 g (0.05 mole) of ethyl 2,2,15,15-tetramethyl-3,14-dithia-1,16-hexadecanoate in 50 ml of tetrahydrofuran was introduced over 17 minutes, in a dry apparatus under a nitrogen atmosphere, into a suspension of 3.8 g (0.1 mole) of LiAlH$_4$ and 75 ml of tetrahydrofuran. The mixture was heated to 60° C throughout 3 hours 35 minutes and then cooled and 11.7 ml of ethyl acetate and 100 ml of 4N hydrochloric acid were poured in.

After filtering off the insoluble material, eliminating the tetrahydrofuran under reduced pressure and extracting with ether, 15.7 g of white crystals are obtained. These crystals were purified by washing with petroleum ether to give 13.9 g of white crystals insoluble in water.

MP$_{inst}$ = 50° C.
Yield = 80%.

EXAMPLE 2

1,8-Bis(2-hydroxyethyl-thio)-octane, alternative name: 3,12-dithia-1,14-tetradecanediol

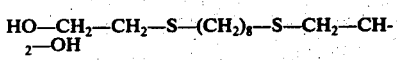

Code No. CRL 40 077

40.5 ml of 10 N caustic soda solution was poured over 10 minutes into a solution of 50 g (0.184 mole) of 1,8-dibromooctane and 31.6 g (0.405 mole) of mercapto-ethanol in 100 ml of ethanol. The temperature of the reaction medium attained the reflux temperature. The mixture was agitated for 1 hour whilst at the ambient temperature (15°-25° C). After eliminating the ethanol under reduced pressure, taking up the residue in water and extracting the insoluble material with chloroform, 49 g of a white powder was obtained. This powder was purified by recrystallisation from ethyl acetate to give 43 g of a white powder insoluble in water and soluble in alcohol.

MP$_{inst}$ (Koefler) = 59° C.
Yield = 93%.

EXAMPLE 3

1,6-Bis(2-hydroxyethyl-thio)-hexane, alternative name: 3,10-dithia-1,12-dodecanediol

Code No. CRL 40 085

43 ml of 10 N caustic soda solution was poured over 20 minutes into a solution of 0.1965 mole of 1,6-dibromohexane and 33.8 g (0.4323 mole) of mercapto-ethanol in 125 ml of ethanol. The reaction medium was heated to 70° C. It was agitated for 45 minutes whilst at the ambient temperature (15°-25° C). After eliminating the ethanol under reduced pressure, taking up the residue in water and extracting the insoluble material with chloroform, 49.1 g of a product in the form of white blocks was obtained. These blocks were purified by recrystallisation from ethyl acetate to give 41 g of a white powder which was insoluble in water and soluble in alcohol.

MP$_{inst}$ (Koefler) = 47° C.
Yield = 88%.

EXAMPLE 4

1,9Bis(2-hydroxyethylthio)-nonane, alternative name: 3,13-dithia-1,15-pentadecanediol

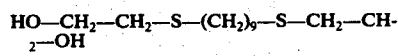

Code No. CRL 40 116

33 ml of 10 N caustic soda solution was poured over 5 minutes into a solution of 0.15 mole of 1,9-dibromononane and 0.33 mole of mercapto-ethanol in 120 ml of ethanol. The temperature of the reaction medium attained 70° C and it was left at the ambient temperature while agitating for 1 hour. After eliminating the ethanol under reduced pressure, taking up the residue in water and extracting the insoluble material with chloroform, 48.7 g of a white powder was obtained. This powder was purified by recrystallisation from ethyl acetate to give 42.2 g of a white powder which was insoluble in water and soluble in alcohol.

MP$_{inst}$ (Koefler) = 64° C.
Yield = 100%

EXAMPLE 5

1,7-Bis(2-hydroxyethyl-thio)-heptane, alternative name: 3,11-dithia-1,13-tridecanediol

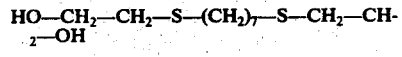

Code No. CRL 40 120

2.6 ml of 10 N caustic soda solution was poured over 10 mins into a solution of 0.121 mole of 1,7-dibromoheptane and 0.266 mole of mercapto-ethanol in 100 ml of ethanol. The temperature of the reaction medium attained 70° C and it was left at the ambient temperature under agitation for 1 hour. After eliminating the ethanol under reduced pressure, taking up the residue in water and extracting the insoluble material with chloroform, 34 g of a white powder was obtained. This powder was purified by recrystallisation from ethyl acetate to give 26.5 g of an oderiferous white crystalline powder, which was insoluble in water and soluble in alcohol.

MP$_{inst}$ (Koefler) = 50° C.
Yield = 87%.

EXAMPLE 6

(±)-2,15-Dimethyl-3,14-dithia-1,16-hexadecanediol

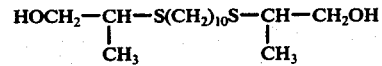

Code No. CRL 40 122

A solution in tetrahydrofuran of 7 g (0.0200 mole) of (±)-2,15-dimethyl-3,14-dithia-1,16-hexadecanedioic acid was slowly poured under a current of nitrogen into an agitated suspension of 2.3 g (0.0605 mole) of LiAlH$_4$ in tetrahydrofuran. The reaction medium was then heated under reflux for 3 hours 15 mins. After neutralisation of the excess reducing agent with ethyl acetate and aqueous alkali, the reaction mixture was filtered and then the solvents were eliminated from the filtrate. The residue was separated between water and methylene chloride. The organic phase was recovered and then washed to neutrality and dried. The solvent was evaporated under reduced pressure and the residue was washed by trituration with petroleum ether. After filtration, 5.4 g of a white crystalline powder was obtained which was insoluble in water. (H is understood that the (+) and (−) isomers can be separated from the racemic form by known methods).

$MP_{inst}$ (Koefler) = 47°–48° C.
Yield = 83.7%

EXAMPLE 6A

Industrial method of preparation of (±)-2,15-dimethyl-3,14-dithia-1,16-hexadecanediol Code No. CRL 40 122 a. Synthesis of 2-methylthiirane

Primary materials

| | |
|---|---|
| Thiourea | 2.79 kg (36.75 moles) |
| Propylene oxide | 2.03 kg, say 2.45 l (35 moles) |
| Water | 23.00 l |
| Sulphuric acid, d = 1.83 | 1.03 l (19.25 moles) |
| Na CO | 3.71 kg (35 moles) |

Equipment

A 50 l reactor equipped with an agitation device, a cooling arrangement, and a 5 l pouring flask; a 50 l decanter.

Operating details

Charge the 50 l reactor with 12.5 l of water and 1.03 l of sulphuric acid (d = 1.83). Cool and add 2.79 kg of thiourea. Agitate in order to dissolve, and cool the liquid mass to 2° C. Then run in slowly 2.03 kg of propylene oxide over about 2 hours, maintaining the temperature between 0° and 5° C. (the reaction is exothermic). Maintain the agitation for a further 2 hours still keeping between 0° and 5° C. Then heat to attain ambient temperature (20° to 25° C) and maintain at that for a further 2 hours. Slowly run in the solution of 3.75 kg of sodium carbonate dissolved in 10 l of water (there is a risk of foaming at first). Agitate for 1 hour after the end of pouring and then allow to decant, Separate the floating liquid (1.810 kg). One can extract the aqueous phase with pentane, but the operation is of little interest because the 2-methylthiirane boils at a low temperature (75° C under 760 mm Hg pressure) and a greater part of it is lost at this concentration.

Wash the floating liquid with 500 cm³ water and dry it over sodium sulphate (500 g), taking care at each time to keep it in a closed vessel because of its volatility and disagreeable odour.

Yield and Characteristics

After drying over sodium sulphate and filtration to remove the sodium sulphate, the following is obtained:

1.715 kg of crude product, i.e. 23.2 moles
Yield (relative to propylene oxide) = 66.3%
$n_D^{20}$ = 1.4762
boiling point 760 mm Hg { 65° – 75° C (95%)

-continued over 75° C (5%)

The fraction distilling between 71° and 74° C represents 90% of the 2-methylthiirane. This crude product is perfectly suited for the following reaction; there is therefore no need to distil it.

b. Synthesis of 2-acetylmercaptopropyl acetate

Primary materials

| | |
|---|---|
| 2-methylthiirane | 1.715 kg (23.2 moles) |
| acetic anhydride | 2.930 kg (29 moles) |
| pyridine | 200 cm³ |
| pulverised ice | 13 kg |
| methylene chloride or chloroform | 12 l |
| sodium bicarbonate | 1 kg |

Equipment 10 l reactor with agitation and reflux refrigeration;
a 10 l heated reactor;
a 30 l tank with agitation;
a 30 l decanter;
a distillation apparatus equipped with an adiabetic column (of 25 mm diameter, 45 cm height, and having "multiknit" packing);
a Perkin separator and a 6 l boiler;
a vacuum pump and manometer.

Method of operation

Charge the 10 l reactor with 2.93 kg of acetic anhydride, 1.715 kg of 2-methylthiirane and 200 cm³ of pyridine. Heat to attain reflux at about 87° C. The temperature rises slowly to 100° C over about 3 to 4 hours. Keep at this temperature until about 6 hours from the start of reflux.

After this time raise the temperature of 130° C and keep it there for 3 to 4 hours. Let the mixture cool to 30° to 40° C and pour the brown-black reaction mixture in a tank containing 13 kg of pulverized ice. Agitate for 1 to 2 hours and then add 6 l of methylene chloride (or chloroform). Agitate for 30 minutes and allow to settle. Separate the organic phase. Carry out two fresh extractions with 2 × 3 l of methylene chloride. Reunite all the organic phases and wash them with 5 l of water then with 2 × 5 l of 100 g/l aqueous solution of bicarbonate. Then rinse twice with 2 l of water. Remove the methylene chloride (or chloroform) under reduced pressure without exceeding 40° C. 4.45 kg of crude product, in the form of a black oil, are obtained. This black oil is distilled under 14 mm Hg.

Each fraction (cf. Table II) is chromatographed on a silica plate (Kieselgel 60-$F_{254}$), eluted by a mixture of toluene-ethyl formate-formic acid (50:40:10) v/v.

Developer: sulphuric vanillin
$R_F$ and coloration = -ester = 0.825 yellow-green
-impurity = 0.910 red The proportion of product expected in each fraction is determined by measuring the refractive index of the distillate. The result is compared with a curve established with mixtures of known quantities of pure 2-acetylmercapto propyl acetate and with pure isolated impurity (which has not yet been identified).

TABLE II

| fraction numbers | 1 | 2 | 3 | 4 | 5 | 6 | 7 | 8 | Residue |
|---|---|---|---|---|---|---|---|---|---|
| P in mmHg | 14 | 14 | 14 | 14 | 14 | 14 | 14 | 14 | |
| Temperature, °C | 32–99 | 99–100 | 100–101 | 101–102 | 102–102 | 102–103 | 103–103,5 | 103,5–105 | no longer distils |
| Quantities recovered | 25 g | 33 g | 282 g | 1130 g | 845 g | 322 g | 159 g | 67 g | 660 g |
| $n_D^{20}$ | 1,4627 | 1,4655 | 1,4660 | 1,4665 | 1,4665 | 1,4665 | 1,4685 | 1,4695 | not measureable |
| Number of bands on chromatography plate | 3 | 1 | 2 | 2 | 2 | 2 | 2 | 2 | 5 |
| % acetate (a) | | 100 | 99 | 98 | 98 | 98 | 94 | 92 | |

(a) 2-acetylmercaptopropyl acetate

Yield and Characteristics

Fractions 2, 3, 4, 5, 6, 7 and 8 are mixed. A clear colourless liquid is obtained ($n_D^{20} = 1,4670$; titre by $n_D^{20} = 97\%$)

Total weight = 2.838 kg; weight of pure product = 2.750 kg (i.e. 15.65 moles)

Yield relative to 2-methylthiirane = 67.5%
Yield relative to propylene oxide = 44.8% c. Synthesis of mercapto-2 propanol

Primary materials

| | |
|---|---|
| 2-acetylmercaptopropyl acetate (97%) | 2.838 kg (15.65 moles) |
| 1% hydrochloric methanol { anhydrous methanol / gaseous hydrogen chloride | 6.5 l / 65 g |
| anhydrous sodium carbonate | 106 g |

Equipment 10 l reactor with agitation and with reflux refrigeration;
heated 10 l reactor;
a sintered glass filter, porosity 2, diameter 185 mm;
a distillation apparatus identical to that in (b).

Operating Method

Charge in the 10 l reactor 6.5 l of anhydrous methanol with 1% hydrochloric acid and 2.838 kg of 2-acetylmercapto-propyl acetate. Heat to attain reflux and maintain thus for 5 hours. One can follow the progress of the reaction chromatographically under the same conditions as in the preceding distillation. Cool. Add 106 g of anhydrous sodium carbonate and agitate for a half hour. Filter the mineral salts.

The methanolic solution thus obtained is concentrated under reduced pressure, and the product is rectified under 20 mm Hg absolute pressure.

As previously, each fraction is chromatographed on a silica plate (Kieselgel 60-$F_{254}$) and eluted with a mixture of toluene-ethyl formate-formic acid (50:40:10) v/v.

Developer: sulphuric vanillin.
$R_F$ and coloration: 2-mercapto-propanol = 0.625, yellow-green The proportion of 2-mercapto propanol in each fraction (compare with Table III, hereafter), is determined by measuring the refractive index of the distillate. The result is compared with a curve established by a mixture of known quantities of 2-mercapto-propanol and methanol.

TABLE III

| Fraction numbers | 1 (b) | 2 | 3 | 4 | 5 | Residue |
|---|---|---|---|---|---|---|
| P in mmHg | 95–50 | 50–30 | 30–20 | 20 | 20 | |
| Temperature, °C | 20–25 | 25–34 | 34–58,5 | 58,5–61 | 61–61,5 | no longer distils |
| Quantities recovered | 4 to 5 l | 125 g | 70 g | 862 g | 135 g | 386 g |
| $n_D^{20}$ | 1,3400 | 1,3767 | 1,4470 | 1,4810 | 1,4820 | not measurable |
| Number of bands on chromatography plate | (a) | 1 | 1 + 1 very small | 1 + 1 very small | 1 + 1 very small | 9 |
| % of 2-mercaptopropanol | | 35 | 80,5 | 99 | 99,5 | |

(a) a very small band of 2-mercaptopropanol
(b) Eraction 1 consists of a mixture of methyl acetate and methanol comprising 2 to 4% 2-mercaptopropanol

Yield and Characteristics

Fractions 3, 4 and 5 are mixed. A colourless clear liquid is obtained.
$n_D^{20} = 1.4975$
titre by $n_D^{20} = 98\%$
total weight: 1.067 kg; weight of pure product 1.045 kg (i.e. 11.37 moles).
Yield relative to the ester: 72.6%
Yield relative to propylene oxide: 32.5% d. Condensation with 1,10-dibromodecane

The procedure is as shown in Example 2, the reaction of 2-mercaptopropanol with 1,10-dibromodecane.

EXAMPLE 7

1,10-Bis(2,3-dihydroxypropyl-thio)decan, alternative name: 4,15-dithia-1,2,17,18-tetrahydroxyoctadecane

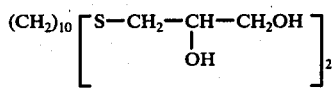

Code No. CRL 40 155

14.4 ml (0.144 mole) of 10 N caustic soda solution was poured over 5 mins into a solution of 18 g (0.060 mole) of 1,10-dibromodecane and 15.7 g (0.144 mole) of 1-mercapto-2,3-propanediol in 60 ml of ethanol. After heating for 1 hour under reflux, evaporating the solvent under reduced pressure and taking up the residue in water, 20.6 g of a white powder was obtained after filtration and water-washing of the precipitate. This powder was purified by recrystallisation from ethanol to give 18 g of a white powder insoluble in water.
$MP_{inst}$ (Koefler) = 95° C.

Yield = 85%

EXAMPLE 8

1,18-Dihydroxy-3,16-di(hydroxymethylene)-4,15-dithia-octadecane

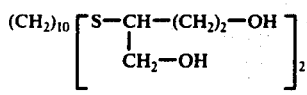

Code No. CRL 40 176 a. Methyl 1,10-decamethylene-dithiomalate

A solution of 14.7 g (0.0335 mole) of 1,10-decamethylene dithiomalic acid, 16 ml (0.4020 mole) of methyl alcohol and 0.75 ml of sulphuric acid in 100 ml of dichloroethane was heated under reflux (80° C) for about 12 hours. The aqueous phase which formed was decanted and the organic phase was washed with water to obtain, after evaporation of the solvent, 16.10 g of a clear colourless oil. After purification by washing in petroleum ether and filtration, 14.8 g of a white powder insoluble in water was obtained.

$MP_{inst}$ (Koefler) = approximately 55° C.
Yield = 89.5%.

b. CRL 40 176

13.5 g (0.0273 mole) of the foregoing diacid in solution in 50 ml of tetrahydrofuran was poured over 45 mins in order to maintain a slight reflux into a suspension of 4.15 g (0.1092 mole) of $LiAlH_4$ in 50 ml of tetrahydrofuran. The mixture was heated under reflux for 5 hours 30 mins and then the excess $LiAlH_4$ was eliminated by 21.5 ml (0.2184 mole) of ethyl acetate and the mixture was hydralysed in the cold by 100 ml of a 4N aqueous solution of hydrochloric acid. After eliminating the tetrahydrofuran under reduced pressure, the insoluble material from the aqueous phase was extracted by warm chloroform to give, after evaporation of the solvent, 8.25 g $MP_{inst}$ (Koefler) = approximately 55° C. of a beige powder.

After purification of 7.25 g of this powder by two successive recrystallisations from ethyl acetate and acetone, 4.6 g of a white powder insoluble in water was obtained.

$MP_{inst}$ (Koefler) = 73° C.
Yield of Stage B = 47.2%. Total yield = 42.2%.

EXAMPLE 9

2,14-Dimethyl-3,13-dithia-1,15-pentadecanediol

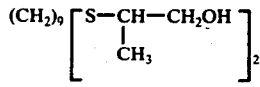

Code No. CRL 40 193 a. 2,14-Dimethyl-3,13-dithia-1,15-pentadecandioic acid 22.4 ml (0.224 mole) of 10 N caustic soda was poured over 5 minutes between 22° and 65° C into a solution of 0.051 mole of 1,9-dibromo-nonane in 75 ml of ethanol. The ethanol was then azeotropically distilled so as to be replaced by the same amount of water. After filtering the solution obtained in the presence of carbon (CXA black), acidifying with dilute hydrochloric acid and extracting the precipitate with ether, 17.3 g of a white powder was obtained. This powder was purified by washing with petroleum ether to give 15.7 g of a white powder insoluble in water.

$MP_{inst}$ (Koefler) = 50° C.
Yield = 92%.

b. CRL 40 193

A solution of 14.5 g (0.043 mole) of the foregoing diacid in 75 ml of ethyl ether was poured over 55 mins into a suspension of 7.4 g (0.194 mole) of $LiAlH_4$ in 30 ml of ethyl ether. After heating for 2 hours under reflux, the excess hydride was neutralised by ethyl acetate and the product was hydrolysed by dilute hydrochloric acid. The organic phase was decanted, washed with a 2 N aqueous caustic soda solution, dried and taken to dryness to give 11.85 g of a pale yellow oil.

After purification of this oil by chromatography over an alumina column, 7.5 g of a colourless oil was obtained which was insoluble in water and which recrystallised on cooling.

Yield of Stage B = 58.8%; total yield = 54%.

The (+) and (-) isomers can, of course, be separated from the racemic form by known methods.

EXAMPLE 10

1,11-Bis-(2-hydroxyethyl-thio)-undecane, alternative name: 3,15-dithia-1,17-heptadecanediol

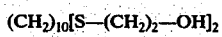

Code No. CRL 40 194

33 ml (0.33 mole) of 10 N caustic soda was poured over 15 mins at 20° to 70° C into a solution of 4.7 g (0.15 mole) of 1,11-dibromoundecane and 25.7 g (0.33 mole) of mercapto ethanol 125 ml of ethanol. The mixture was agitated for 45 minutes at the ambient temperature (15°-25° C) and the ethanol was eliminated under reduced pressure. After extracting the insoluble material with chloroform, washing the organic phase with water and evaporating the solvent, 45.6 g of a white powder was obtained This powder was purified by recrystallisation from ethyl acetate to give 43.1 g of a white powder insoluble in water.

$MP_{inst}$ (Koefler) = 73° C.
Yield = 93.5%.

The compounds of the invention have hypolipaemiant and hypocholesterolaemiant properties and are thus useful in therapeutics, particularly in the treatment of hyperlipaemia and hypercholesterolaemia. According to the invention, therapeutic compositions are provided which contain in association with a physiologically-acceptable excipient at least one compound of Formula I.

The results of pharmacological tests which have been carried out are given below. This summary relates particularly to two of the compounds of the series, CRL 40 055 (Example 1) and CRL 40122 (Example 6) which have proved to be particularly interesting, CRL 40122 being, according to the invention, the preferred product.

In Table IV below the following results have been obtained.

A — in rats receiving a normal diet (percentage inhibition = 100%);

B — in rats receiving a hyperlipidic diet (percentage inhibition = 0%);

C — in rats receiving the same hyperlipidic diet B with a daily dose of 0.1 g/kg of a reference normolipidemiant LIPAVLON [ethyl-2-(p-chlorophenoxy)-2-methylpropionate; International name: CLOFIBRATE];

D — in rats receiving the same hyperlipidic diet B with a daily dose of 0.1 g/kg of a reference normolipidemiant ATHEROLIP [aluminium salt of 2-(p-chlorophenoxy)-2-methylpropionic acid];

E — in rats receiving the same hyperlipidic diet B with a daily dose of 0.1 g/kg of a reference normolipidemiant, LL 1558 [1,10-bis(2-hydroxyethyl-thio)decane];

F — in rats receiving the same hyperlipidic diet B with a daily dose 0.010 g/kg, 0.025 g/kg or 0.050 g/kg of CRL 40046.

The averages of the tests effected on CRL 40 055 in three different doses and calculated comparatively to reference products corresponding to various experiments allow an activity of the product to be concluded as follows:

in a dose of 0.050 g/kg, the percentage of inhibition is 40% to 60% depending on the dosage;

in a dose of 0.025 g/kg, the percentage is still between 30% and 55%, in a dose of 0.010 g/kg, the activity appears to have completely disappeared.

A dose of 0.025 g/kg appears to be particularly interesting because at this level the product CRL 40055 appears to provide a substantially constant activity as compared with the reference products utilised in a dose of 0.1 g/kg.

Results relating to CRL 40 122

The product is not toxic. The experiments relating to acute toxicity by oral dose for mice and rats have given evidence that there is no mortality amongst animals treated up to a dose of 5 g/kg.

The hypolipaemiant properties of the CRL 40 122 have been studied in rats according to two different standard experiments:

A study on Wistar rats subjected to a hyperlipidic diet (standard I); and

A study on normal Wistar rats (standard II).

The results obtained according to these two standards are in agreement.

Experimetal standard I

The experiment was conducted for two weeks on Wistar rats, subjected to a daily hyperlipidic diet at the dose of about 20 g for an animal of 150 g in average.

The activity of the product studied was determined by comparison with normal control groups of rats and with groups of rats subjected to a hyperlipidic diet and not treated. For each dose of CRL 40 122 there were three groups of five animals each (control group, group only receiving the hyperlipidic diet, and treated group). The results obtained correspond to the average of each of the series. A very interesting activity of CRL 40 122 appeared at active doses of 10 mg to 50 mg/kg in rats subjected to a hyperlipidic diet (decrease from 64 to 34% of the rate of blood lipids according to dose; decrease of cholesterol from 68 to 41%).

Experimetal standard II

The experiment was carried out over five days on normal male Wistar rats. The animals, numbering 8 per dose of the product to be studied, were treated orally daily, the last feed taking place 3 hours before the animals were killed. Each series was divided into two groups of animals: one group killed after 3 days of experiment; the other group killed after 5 days of experiment.

The results were determined by comparison with 8 normal rats subjected to the same experimental conditions and not treated. A decrease of 31% in total lipids and 23% in cholesterol was observed for an oral dose of 20 mg/kg.

Overall these tests led to the following conclusions:
1. The two experimental standards, although very different give rise to a product activity of the order of:
   60% for a dose of 50 mg/kg
   30% for a dose of 20 mg/kg
   20% for a dose of 10 mg/kg
2. The activity of the product appears after the third day of treatment.

In human therapeutics, CRL 40 122 has been used with success in the form of capsules dosed at 100 mg and at 200 mg. Patients suffering from hyperlipaemia and hypercholesterolaemia and who have received a total dose of 400 mg per day of the active principle have seen their hyperlipaemia and their hypercholesterolaemia decrease after several days of treatment.

TABLE I $(CH_2)_n(S-A-OH)_2$

| Ex. | n | A | Melting Point* °C | Code No. |
|---|---|---|---|---|
| 1 | 10 | $C(CH_3)_2CH_2$ | < 50 | CRL 40 055 |
| 2 | 8 | $CH_2CH_2$ | 59 | CRL 40 077 |
| 3 | 6 | $CH_2CH_2$ | 47 | CRL 40 085 |
| 4 | 9 | $CH_2CH_2$ | 64 | CRL 40 116 |
| 5 | 7 | $CH_2CH_2$ | 50 | CRL 40 120 |
| 6 | 10 | $CH(CH_3)CH_2$ | 47–48 | CRL 40 122 |
| 7 | 10 | $CH_2CHOHCH_2$ | 95 | CRL 40 155 |
| 8 | 10 | $CH(CH_2OH)CH_2CH_2$ | 73 | CRL 40 176 |
| 9 | 9 | $CH(CH_3)CH_2$ | 20 | CRL 40 193 |
| 10 | 11 | $CH_2CH_2$ | 73 | CRL 40 194 |

*Note: The melting points are measured on a Kofler bench ($F_{inst}$)

TABLE IV

| Diet and Product used | Total Lipids g/l | Total Lipids % inhibition | Total Cholesterol g/l | Total Cholesterol % inhibition | Burstein Test g/l | Burstein Test % inhibition |
|---|---|---|---|---|---|---|
| Normal | 2.75 | 100 | 0.7 | 100 | 24 | 100 |
| Hyperlipidic | 10.7 | — | 3.98 | — | 120 | — |
| Hyperlipidic + Atherolip-0,1g/kg | 6.8 | 49 | 2.08 | 59 | 56 | 67 |
| Hyperlipidic + Lipavlon-0,1g/kg | 7.75 | 37 | 2.47 | 46 | 73 | 49 |
| Hyperlipidic + CRL 40 055–0,050g/kg | 7.45 | 41 | 2.29 | 51 | 64 | 58 |
| Normal | 3.93 | 100 | 0.81 | 100 | 28 | 100 |
| Hyperlipidic | 10.5 | — | 4.24 | — | 105 | — |
| Hyperlipidic + Lipavlon-0,1g/kg | 9.2 | 20 | 3 | 36 | 84 | 27 |
| Hyperlipidic + LL 1558–0,1g/kg | 5.1 | 82 | 1.33 | 85 | 38 | 87 |
| Hyperlipidic + CRL 40 055–0,025g/kg | 8.06 | 37 | 2.43 | 53 | 82 | 30 |

TABLE IV-continued

| Diet and Product used | Total Lipids | | Total Cholesterol | | Burstein Test | |
|---|---|---|---|---|---|---|
| | g/l | % inhibition | g/l | % inhibition | g/l | % inhibition |
| Normal | 3.3 | 100 | 0.64 | 100 | 27 | 100 |
| Hyperlipidic | 8.43 | — | 2.98 | — | 93 | — |
| Hyperlipidic + Lipavlon-0,1g/kg | 7.3 | 22 | 1.58 | 60 | 76 | 25 |
| Hyperlipidic + LL 1558-0,1g/kg | 4.5 | 77 | 1.33 | 70 | 37 | 85 |
| Hyperlipidic + CRL 40 055-010g/kg | 11.3 | 0 | 3.81 | 0 | 123 | 0 |

I claim:

1. A therapeutic composition for treatment of hyperlipemia and/or hypocholesterolemia by oral administration comprising a therapeutically effective amount of a compound selected from the group consisting of 2,2,15,15,-tetramethyl-3,14-dithia-1,16-hexadecanediol and 2,15,-dimethyl-3, 14-dithia-1,16 hexadecanediol with a physiologically acceptable excipient.

2. A therapeutic composition as claimed in claim 1 wherein the compound is 2,2,15,15,-tetramethyl-3,14-dithia-1,16-hexadecanediol.

3. A therapeutic composition as claimed in claim 1 wherein the compound is 2,15,-dimethyl-3,14-dithia-1,16-hexadecanediol.

* * * * *